United States Patent
Essayem et al.

(10) Patent No.: US 9,238,635 B2
(45) Date of Patent: Jan. 19, 2016

(54) METHOD FOR PRODUCING 5-HYDROXYMETHYLFURFURAL

(75) Inventors: Nadine Essayem, Saint Just Chaleyssin (FR); Rodrigo Lopes De Souza, Rio de Janeiro (BR); Franck Rataboul, Lyons (FR)

(73) Assignees: CENTRE NATIONAL DE LA RECHERCHE SCIENTIFIQUE (C.N.R.S.), Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 14/117,984

(22) PCT Filed: May 16, 2012

(86) PCT No.: PCT/EP2012/059193
§ 371 (c)(1),
(2), (4) Date: Jan. 8, 2014

(87) PCT Pub. No.: WO2012/156479
PCT Pub. Date: Nov. 22, 2012

(65) Prior Publication Data
US 2014/0121389 A1 May 1, 2014

(30) Foreign Application Priority Data
May 16, 2011 (FR) ..................... 11 54232

(51) Int. Cl.
*C07D 307/48* (2006.01)
*C07D 307/46* (2006.01)
*C07D 307/50* (2006.01)

(52) U.S. Cl.
CPC ............ *C07D 307/48* (2013.01); *C07D 307/46* (2013.01); *C07D 307/50* (2013.01)

(58) Field of Classification Search
CPC ... C07D 307/46; C07D 307/48; C07D 307/50
USPC ........................................ 549/488
See application file for complete search history.

(56) References Cited

U.S. PATENT DOCUMENTS

| | | | |
|---|---|---|---|
| 2,929,823 | A | 3/1960 | Garber et al. |
| 4,740,605 | A | 4/1988 | Rapp |
| 7,572,925 | B2 | 8/2009 | Dumesic et al. |
| 8,242,293 | B2 * | 8/2012 | Gruter et al. ............... 549/501 |
| 2006/0142599 | A1 | 6/2006 | Sanborn et al. |
| 2009/0156841 | A1 | 6/2009 | Sanborn |

FOREIGN PATENT DOCUMENTS

| | | |
|---|---|---|
| CN | 101 381 351 A | 3/2009 |
| CN | 101 381 351 K1 | 3/2009 |
| FR | 2670209 | 6/1992 |
| GB | 600 871 | 4/1948 |

OTHER PUBLICATIONS

Li, Y., "Fructose decomposition kinetics in organic acids-enriched high temperature liquid water." Biomass and Bioenergy 33.9 (2009): 1182-1187.*
Kupiainen, L.,"Kinetics of glucose decomposition in formic acid." Chemical Engineering Research and Design 89.12 (2011): 2706-2713.*
Kupiainen, L.,"Comparison of formic and sulfuric acids as a glucose decomposition catalyst." Industrial & Engineering Chemistry Research 49.18 (2010): 8444-8449.*
Tarabanko, V. E., "High temperature 5-hydroxymethylfurfural synthesis in a flow reactor." Chemistry for Sustainable Development 14.1 (2006): 49-53.*
Mika Ohara, et al., "Syntheses of 5-Hydroxymethylfurfural and Levoglucosan by Selective Dehydration of Glucose Using Solid Acid and Base", 2010, pp. 149-155, vol. 383, Applied Catalysis A.
International Search Report for PCT/EP2012/059193 dated Jun. 21, 2012.
Antal M. J. et al.: "Mechanism and formation of 5-(hydroxymethyl)-2-furaldehyde from D-fructose and sucrose", Carbohydrate Research, vol. 199, 1990, pp. 91-109.
Harworth W. N. and Jones W. G. M.: "The Conversion of Sucrose into Furan Compounds. Part I. 5-Hydroxymethylfurfuraldehyde and Some Y Derivatives", Journal of the Chemical Society, 1944, pp. 667-670.
Chareonlimkun A et al: "Reactions of C5 and C6-sugars, cellulose, and lignocellulose under hot compressed water (HCW) in the presence of heterogeneous acid catalysts", Fuel, IPC Science and Technology Press, Guildford, GB, vol. 89, No. 10, (Oct. 1, 2010), pp. 2873-2880.
Shimizu K I et al: "Enhanced production of hydroxymethylfurfural from fructose with solid acid catalysts by simple water removal methods", Catalysis Communications, Elsevier Science, Amsterdam, NL, vol. 10, No. 14, (Aug. 25, 2009), pp. 1849-1853.
Carniti P et al: "Niobic acid and niobium phosphate as highly aciidic viable catalysts in aqueous medium: Fructose dehydration reaction", Catalysis Today, Elsevier, NL, vol. 118, No. 3-4, (Dec. 15, 2006), pp. 373-378.
Kalpesh B. Sidhpuria, et al: "Supported ionic liquid silica nanoparticles (SILnPs) as an efficient and recyclable heterogeneous catalyst for the dehydration of fructose to 5-hydroxymethylfurfural", Green Chemistry, The Royal Society of Chemistry, 2011, 13 pp. 340-349.
Stahlberg Tim, et al: "Direct conversion of glucose to 5-(hydroxymethyl)furfural in ionic liquids with lanthanide catalysts", Green Chemistry, The Royal Society of Chemistry, 2010, 12(2) pp. 321-325.

(Continued)

*Primary Examiner* — Samantha Shterengarts
*Assistant Examiner* — Matt Mauro
(74) *Attorney, Agent, or Firm* — B. Aaron Schulman, Esq.; Stites & Harbison, PLLC.

(57) ABSTRACT

The invention relates to a method for preparing 5-hydroxymethylfurfural (HMF) by reacting hexose in water and in the presence of carboxylic acid. The present invention further relates to the preparation of 5-hydroxymethylfurfural (HMF) by reacting hexose in water and in the presence of carboxylic acid and of a heterogenous acid catalyst. The invention also relates to an HMF-rich carboxylic acid solution.

19 Claims, 10 Drawing Sheets

(56) References Cited

OTHER PUBLICATIONS

Thomas S. Hansen, et al: "Synergy of boric acid and added salts in the catalytic dehydration of hexoses to 5-hydroxymethylfurfural in water", Green Chemistry, The Royal Society of Chemistry, 2010, 13(1) pp. 109-114.

Juben N. Chheda, et al: "Production of 5-hydroxymethylfurfural and furfural by dehydration of biomass-derived mono- and poly-saccarides", Green Chemistry, The Royal Society of Chemistry, 2007, 9 pp. 342-350.

* cited by examiner

METHOD FOR PRODUCING 5-HYDROXYMETHYLFURFURAL

The present invention relates to the preparation of 5-hydroxymethylfurfural (HMF) by dehydration of hexose or derivatives thereof or products including hexoses or hexose derivatives.

HMF and its principle derivative, furandicarboxylic acid (FDCA) are molecules having an enormous potential, in particular for the production of polymers, in particular polyamides or polyesters, because of their structural similarities with terephthalic acid, a monomer usually used.

HMF can be obtained by dehydration, in an aqueous medium, of carbohydrates, in particular fructose, glucose or cellulosic material. However, the yield and selectivity are low, in particular in purely aqueous media.

The lack of HMF selectivity of the carbohydrate dehydration reaction is explained by the rapidity of the secondary polymerization reactions of the reaction intermediates or of the HMF in a purely aqueous medium (for example, the formation of humin).

Different processes have been developed in order to attempt to improve the conversion of carbohydrates and the HMF selectivity.

From FR2670209, we know the preparation of HMF by dehydration of fructose in an aqueous medium, in the presence of an acid catalyst and an extraction solvent, enabling the HMF formed to be extracted from the aqueous medium in order to limit its degradation. The best yield obtained is 32% and the HMF selectivity is low. Levulinic acid may also be a significant by-product of the dehydration of fructose formed by HMF degradation in the case of an excessively acidic reaction medium and, more generally, excessively severe reaction conditions.

We also know, from Antal et al. (Carbohydrate Research, 1990, 199, 91-109), a process for preparing HMF in an aqueous medium including low organic acid concentrations (catalytic quantities of less than 5% by weight). The HMF yield is, however, very low.

The use of a biphasic medium, consisting of a reactive aqueous phase containing water and dimethylsulfoxide (DMSO) and an acid catalyst and an extraction phase (enabling the HMF formed to be extracted from the aqueous medium in order to limit its degradation) based on methyl isobutyl ketone (MIBK) and butanol or dichloromethane, for the preparation of HMF from fructose or glucose has also been implemented (WO 2007/146636; Dumesic et al., Green Chem., 2007, 9, 342-350). The use of solvents with a high boiling point such as N-methylpyrrolidone (NMP) and an acid catalyst (US 2006/0142599) has also been proposed. In these processes, the fructose and glucose conversion and the HMF selectivity are high. However, these processes require the use of solvents that may be toxic, therefore necessitating purifications of the HMF obtained, and of which the boiling temperatures are high, making these processes complex and costly.

The use of a weak acid, such as boric acid, associated with the addition of salt and the use of an extraction solvent such as methyl isobutyl ketone is also known. The HMF yields from fructose are 60% (Thomas S. Hansen et al., Green Chem., 2010, 13(1), 109-114).

The use of ionic liquid has also been proposed with a lanthanide-based catalyst (Stählberg et al., Green Chem., 2010, 12(2), 321-325).

Finally, we know, from WO 2009/076627, the preparation of HMF by hydrolysis of its ester obtained from fructose in a column including an Amberlyst-type resin and in the presence of acetic acid. However, a process enabling HMF to be obtained directly from fructose is not described.

Thus, to increase the carbohydrate conversion and the HMF selectivity, increasingly complex techniques have been developed.

The selective production of HMF is complex, and its purification is difficult due to the instability of this molecule. It is also difficult to obtain HMF inexpensively. For these reasons, there is still no industrial-scale production of HMF.

There is therefore an interest in providing a process for preparing HMF that responds to the disadvantages of the processes of the prior art.

An objective of the present invention is to provide a process for preparing HMF that is advantageous from an industrial perspective.

Another objective of the present invention is to provide a process for preparing HMF with a high conversion and selectivity.

Another objective of the present invention is to provide a process for preparing HMF making it possible to reduce, or even eliminate, the formation of by-products, in particular of the humin type.

An objective of the invention is also to provide a process using solvents that are nontoxic and capable of being easily eliminated and/or recycled, with or without catalysts.

Other objectives will appear in view of the following description of the invention.

All of these objectives are satisfied by the invention, which relates to a process for preparing 5-hydroxymethylfurfural (HMF) by reacting hexose in water and in the presence of carboxylic acid.

According to the invention "hexose" refers, in addition to cyclic compounds of chemical formula $C_6H_{12}O_6$ such as glucose or fructose or mixtures thereof, to hexose derivatives and products including hexoses or derivatives thereof. Compositions including hexoses are also covered by the process of the invention.

"Hexose derivatives" refers to compounds including, in their structure, at least one hexose unit, and they may in particular be obtained by hexose polymerization. The hexose derivatives according to the invention are in particular polymers of glucose, in particular starch, cellulose or containing at least one hexose unit, hemicellulose.

According to the invention, the products including hexoses or derivatives thereof can be represented by lignocellulosic biomass, which corresponds to a blend of cellulose, hemicellulose and lignin; or paper, which includes cellulose, in particular recycled paper.

Celluloses, hemicelluloses, lignocellulosic biomass and paper can be used as is in the process of the invention. They may also be pre-treated, in particular by more or less extensive hydrolysis, before being subjected to the step in the presence of carboxylic acid of the invention.

Preferably, the hexose is fructose.

The carboxylic acids can be monoacids, diacids or triacids. They are in particular chosen from:
  acids of formula R—COOH wherein R represents a hydrogen atom or a $C_1$ to $C_5$, preferably $C_1$ to $C_3$, alkyl chain, linear or branched, optionally substituted by one or more OH groups;
  acids of formula HOOC-L-COOH wherein L represents a bond or a $C_1$ to $C_5$, preferably $C_1$ to $C_3$, alkyl chain, linear or branched, optionally substituted by one or more OH and/or COOH groups; or
  mixtures thereof.

Preferably, the carboxylic acid is formic acid, acetic acid, malic acid, citric acid, oxalic acid, lactic acid, propionic acid, or mixtures thereof.

Particularly preferably, the acid is chosen from the acids of formula R—COOH wherein R represents a hydrogen or a $C_1$ to $C_5$, preferably $C_1$ to $C_3$, alkyl chain, linear or branched, optionally substituted by one or more OH groups, and mixtures thereof. Preferably, the carboxylic acid is formic acid, acetic acid, propionic acid, lactic acid or mixtures thereof. More preferably, the carboxylic acid is formic acid, acetic acid, lactic acid or mixtures thereof.

More preferably, the carboxylic acid is formic acid, acetic acid or a mixture thereof. These two acids have the advantage of being stable in the reaction medium and of being easily eliminated in particular by vacuum evaporation.

Advantageously, when the carboxylic acid is formic acid, the conversion of the starting hexose, e.g. fructose, may be complete. It will thus be possible to obtain an HMF-rich formic acid composition that may be used directly, in particular for the preparation of polymer, for example polyamides or polyesters.

Advantageously, when the carboxylic acid is acetic acid, the conversion of the starting hexose, e.g. fructose, and the purification of the HMF obtained is facilitated because of the volatility of the acetic acid. It will thus be possible to obtain an HMF-rich acetic acid composition that may be used directly, in particular for the preparation of polymer, for example polyamides or polyesters; or to purify this solution in order to obtain HMF.

The presence of acid according to the invention, by comparison with the same process implemented only in the presence of water, makes it possible to significantly increase the conversion of hexose, e.g. fructose, and the HMF selectivity.

A person skilled in the art, depending on whether it is preferable to promote the conversion of hexose, e.g. fructose, or the HMF selectivity or have a good compromise between these two characteristics, may determine the proportion and the nature of the acid to be integrated in the reaction medium. The quantity of acid must not be too great due to the risk of increasing the production of by-products, in particular humin.

The inventors demonstrated that the control of the acid concentration makes it possible in a particularly advantageous and surprising manner to obtain a high HMF yield and selectivity. At a low acid concentration, the HMF yield is very low and even nonexistent, and at a high acid concentration the HMF yield is low and the levulinic acid is obtained as a by-product in large amounts.

Thus, preferably, the quantity of acid is between 5 and 80% by weight, in particular between 5 and 70% by weight, more preferably between 10 and 50% by weight, for example 20% or 10% by weight with respect to the total water+carboxylic acid weight.

It was also demonstrated by the inventors that, surprisingly, the carboxylic acids, and in particular formic and acetic acids, in particular acetic acid, made it possible to stabilize the HMF formed in the aqueous medium.

Thus, the HMF obtained in the aqueous acetic acid medium after 3h at 150° C. is degraded only up to 25%, whereas in an acidified medium at the same pH (1.71) by adding HCl, 60% of the HMF is degraded.

In the process according to the invention, water is present preferably in a quantity of between 20 and 95% by weight, preferably between 30 and 95% by weight, for example between 50 and 90% by weight, for example 80 or 90% by weight with respect to the total water+carboxylic acid weight.

In the process of the invention, the quantity of hexose, e.g. fructose, is dependent on its solubility in the water and carboxylic acid mixture. It is generally between 0.5 and 35%, preferably between 1% and 30%, in particular between 0.5 and 25%, preferably between 1 and 15%, for example 1%, with respect to the total water+carboxylic acid weight.

The inventors also showed that the pH could have an influence on the reaction. Thus, if the pH is too acid, a large quantity of by-products, in particular humin, may form.

Advantageously, the pH of the reaction medium at the start of the reaction is between 1 and 3, preferably between 1.5 and 2.5. It is, for example, 1.7.

The process according to the invention can be conducted at a temperature of between 100 and 200° C., preferably between 120 and 180° C., for example between 150 and 180° C.

The process according to the invention can be implemented at an atmospheric pressure or under pressure of an inert gas, for example helium, up to a pressure of 3.5 MPa (i.e. 35 bars).

The process of the invention can advantageously be implemented in the presence of a heterogeneous acid catalyst. Preferably, the catalyst is chosen from tungstophosphoric acid, preferably dispersed on niobium hydroxide (NbOH); niobium hydroxide; sulfated zirconia; acidic cesium salts of tungstophosphoric acid ($Cs_2HPW_{12}O_{40}$); titanium dioxide; sulfonated carbon; functionalized carbon, for example by carboxylic groups, for example after oxidation, for example oxidation with Javel water; or mixtures thereof.

The addition of these catalysts makes it in particular possible advantageously to increase the hexose, e.g. fructose, conversion and the HMF selectivity.

Particularly preferably, the catalyst is a sulfonated carbon or a functionalized carbon.

When it is present, the quantity of catalyst is preferably between 2 and 100% by weight, preferably between 2 and 10% by weight, for example 5% by weight with respect to the weight of hexose, e.g. fructose.

Advantageously, the process of the invention does not require the use of a solvent other than water. Thus, and preferably, the process of the invention is implemented in the absence of an organic solvent.

The process according to the invention can be implemented in batches or continuously. It will advantageously be implemented continuously. If a heterogeneous acid catalyst is used, the process will advantageously be implemented continuously on a fixed-bed catalyst.

Advantageously, the process of the invention makes it possible to obtain hexose, in particular fructose, conversions greater than 50%, preferably greater than 90%.

Advantageously, the process of the invention makes it possible to obtain an HMF selectivity greater than 50%, preferably greater than 75%.

The invention also relates to aqueous carboxylic acid solutions including HMF, preferably including 0.1 to 10% by weight of HMF, for example 0.3 to 6% by weight of HMF and capable of including 0 to 5% by weight of hexose, e.g. fructose, for example 0 to 0.5% by weight of hexose, e.g. fructose. These solutions are capable of being obtained by and owing to the process of the invention.

More specifically, the invention relates to an aqueous formic acid or acetic acid solution including HMF, preferably including 0.1 to 15%, preferably 0.1 to 10% by weight of HMF and capable of including 0 to 5% by weight of hexose, e.g. fructose. Preferably, this solution does not include hexose, e.g. fructose, and can be used directly, in particular for the preparation of polymers such as polyamides and polyesters.

The present invention will now be described using non-limiting examples.

EXAMPLE 1

Influence of Carboxylic Acid

The synthesis of HMF is performed in a 100-ml autoclave. The following quantities are introduced into the reactor: 60 g of aqueous solution, 0.6 g of fructose.

The aqueous solutions used are pure or include carboxylic acids. The aqueous carboxylic acid solutions have the following compositions:

12 g of lactic acid added to 48 g of distilled water; or
12 g of acetic acid added to 48 g of distilled water; or
12 g of formic acid added to 48 g of distilled water. 2 MPa (20 bars) of helium are introduced into the autoclave. The reaction medium is stirred with a magnetic stirrer. The reaction medium is brought to the reaction temperature by means of electrical resistances set at 150° C. After 2 hours of reaction at 150° C., the autoclave is cooled by means of an ice bath. The fructose conversion and the HMF molar yield are determined by HPLC-RID analysis (column: COREGEL 87C).

Figure 1:
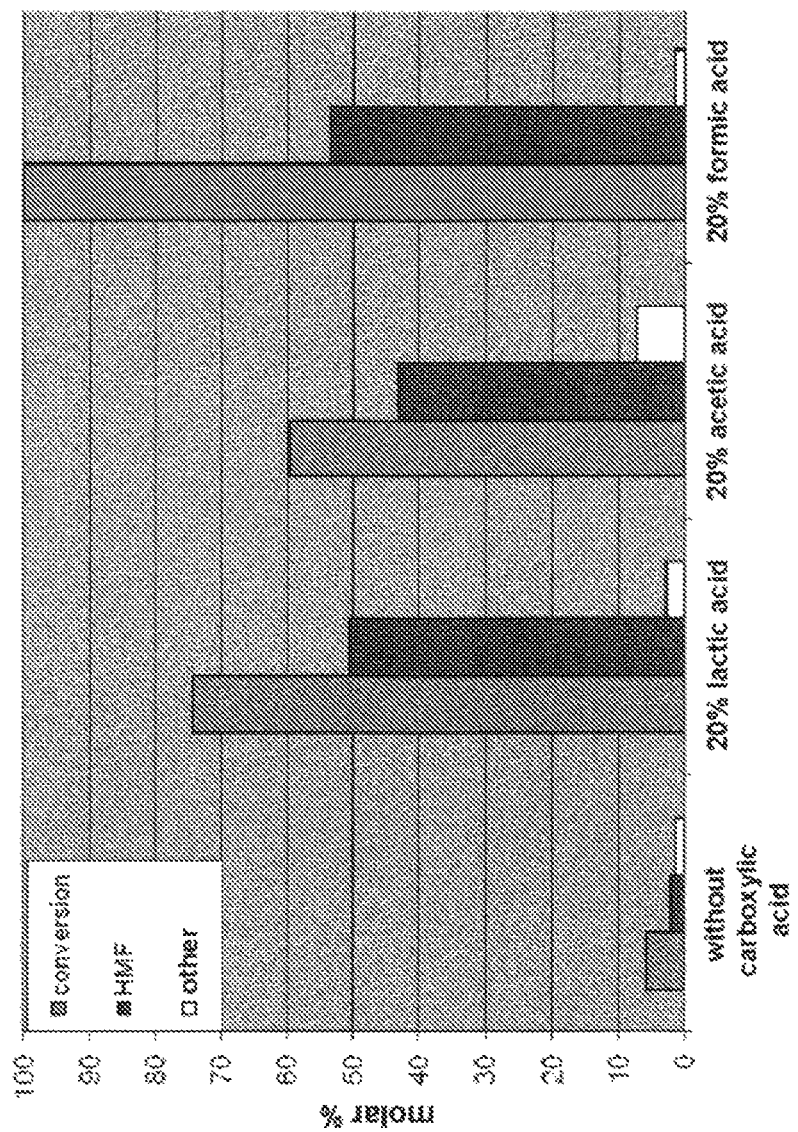
FIG. 1 shows the influence of the nature of the carboxylic acid added to the aqueous medium on the fructose conversion at 150° C. (Ac=acid; AcAc=acetic acid).

The results obtained are shown in FIG. 1. The results show that the addition of carboxylic acid makes it possible to increase the fructose conversion and the HMF selectivity. The results also show that the fructose conversion is complete with formic acid and that the best compromise between conversion and HMF selectivity is obtained with acetic acid.

EXAMPLE 2

Influence of the Addition of Heterogeneous Acid Catalysts

The synthesis of HMF is performed in a 100-ml autoclave. The following quantities are introduced into the reactor: 48 g of distilled water, 12 g of acetic acid, 0.6 g of fructose, 30 mg of catalyst. 2 MPa (20 bars) of helium are introduced into the reaction medium. The reaction medium is stirred by means of a magnetic stirrer. The reaction medium is brought to the reaction temperature by means of electrical resistances set at 150° C. After 2 hours of reaction at 150° C., the autoclave is cooled by means of an ice bath. The catalyst is separated by filtration. The fructose conversion and the HMF molar yield are determined by HPLC-RID analysis (column: COREGEL 87C).

The process was implemented in the absence of catalyst and in the presence of different catalysts, namely tungstated zirconia (ZrW), acidic cesium salts of tungstophosphoric acid ($Cs_2H$: $Cs_2HPW_{12}O_{40}$); titanium dioxide ($TiO_2$), sulfonated carbon (C/Sulfonated), niobium hydroxide (NbOH) and carbon functionalized by carboxylic groups after oxidation with Javel water.

Figure 2:
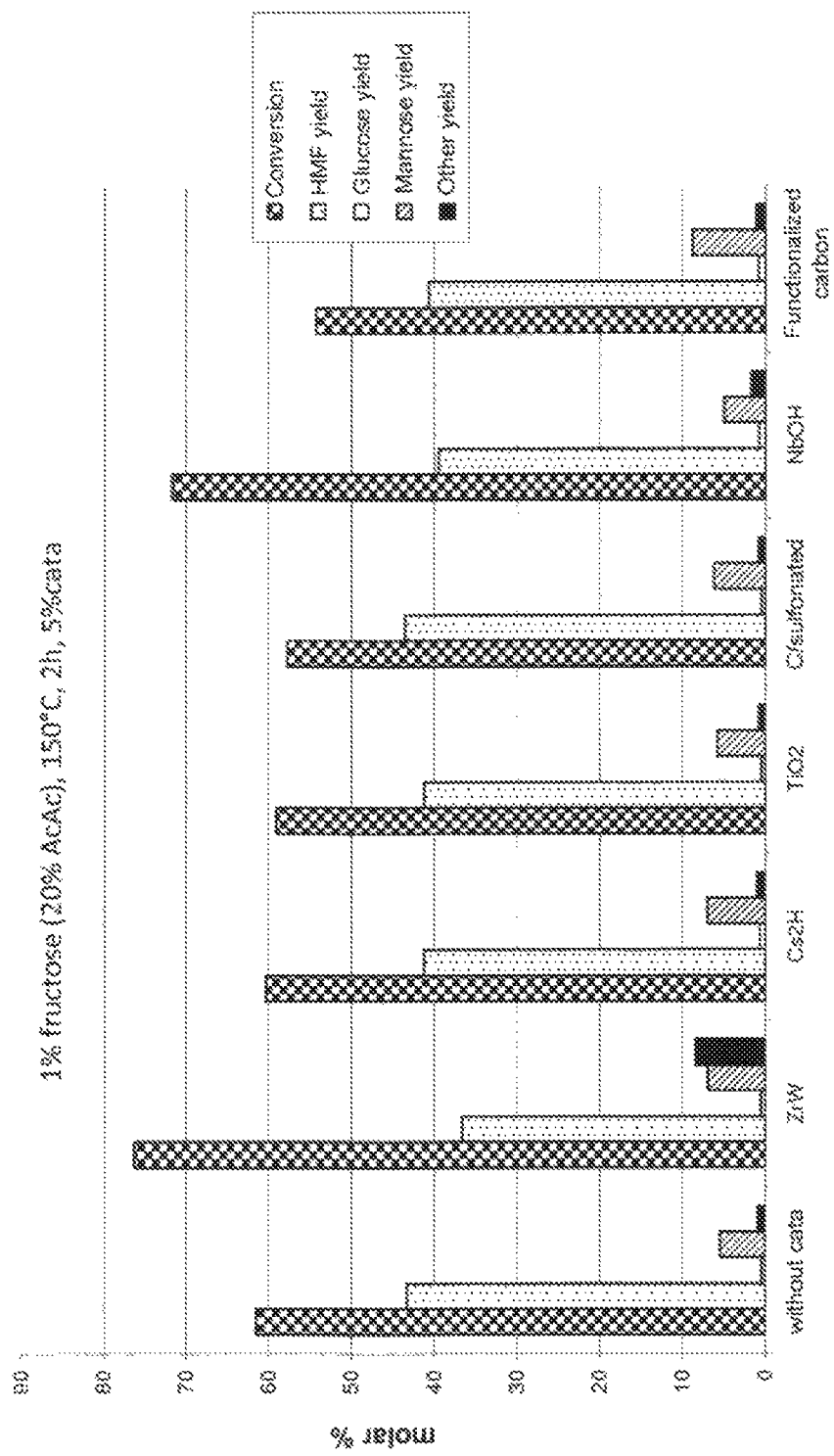
FIG. 2 shows the influence of the nature of the heterogeneous catalyst added to the aqueous acetic acid solution on the fructose conversion and the HMF yield at 150° C.

The results obtained are shown in FIG. 2. The results show that the addition of catalyst makes it possible to increase the fructose conversion. The results show in particular that the best compromise between conversion and HMF selectivity is obtained with sulfonated carbon or functionalized carbon.

EXAMPLE 3

Influence of the Carboxylic Acid Content

The synthesis of HMF is performed in a 100-ml autoclave. The following quantities are introduced into the reactor: 60 g of distilled water or 60 g of an aqueous solution capable of containing 5%, 10%, 20%, 30% and 50% by weight of carboxylic acid or 60 g of pure carboxylic acid and 0.6 g of fructose. 2 MPa (20 bars) of helium are introduced into the autoclave. The reaction medium is stirred by means of a magnetic stirrer. The reaction medium is brought to the reaction temperature by means of electrical resistances set at 150° C. After 2 hours of reaction at 150° C., the autoclave is cooled by means of an ice bath. The fructose conversion and the HMF molar yield are determined by HPLC-RID analysis (column: COREGEL 87C).

Figure 3:
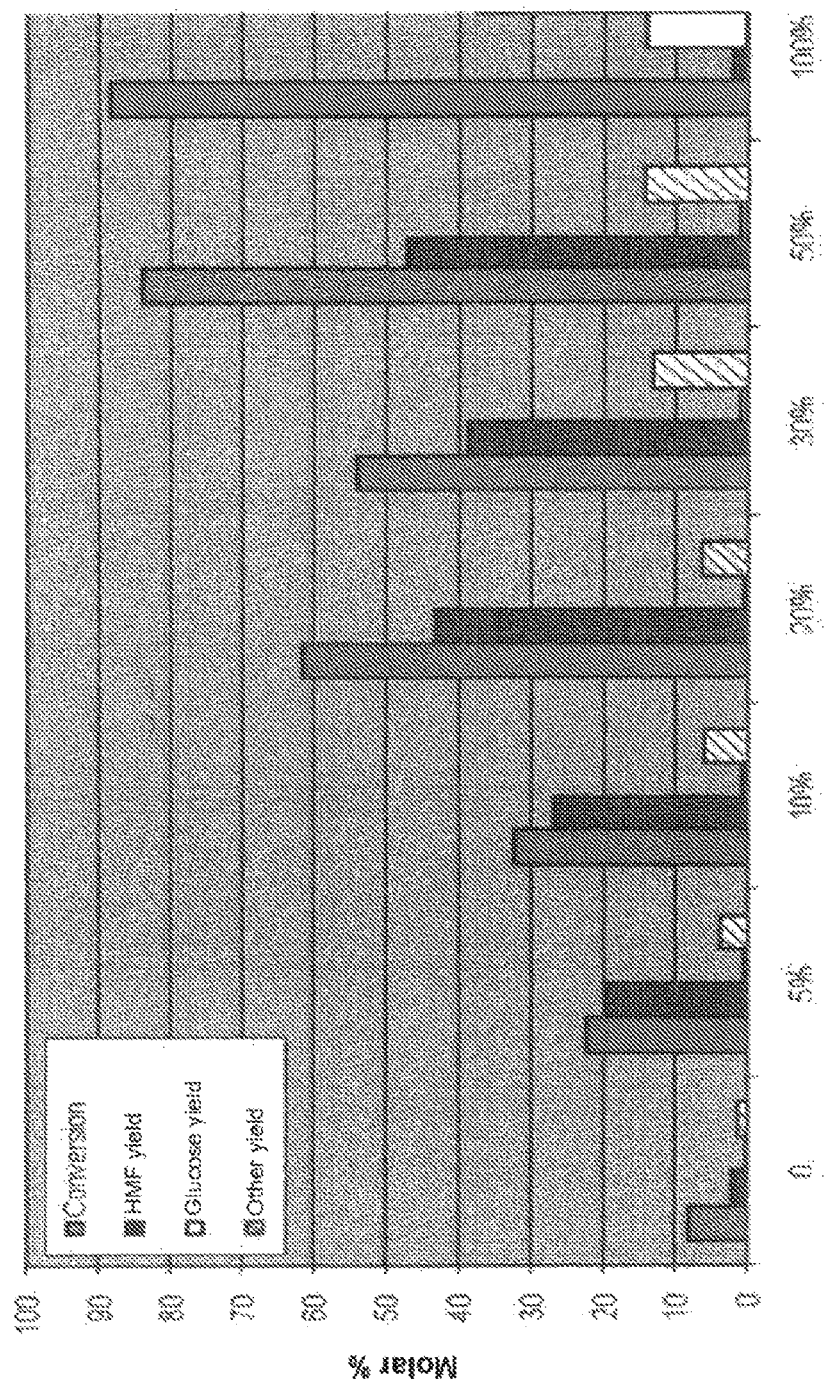
FIG. 3 shows the influence of the acetic acid content in the aqueous reaction medium on the conversion of fructose into HMF in the absence of the addition of a heterogeneous catalyst at 150° C. (Yield=yield; cata=catalyst).
Figure 4:
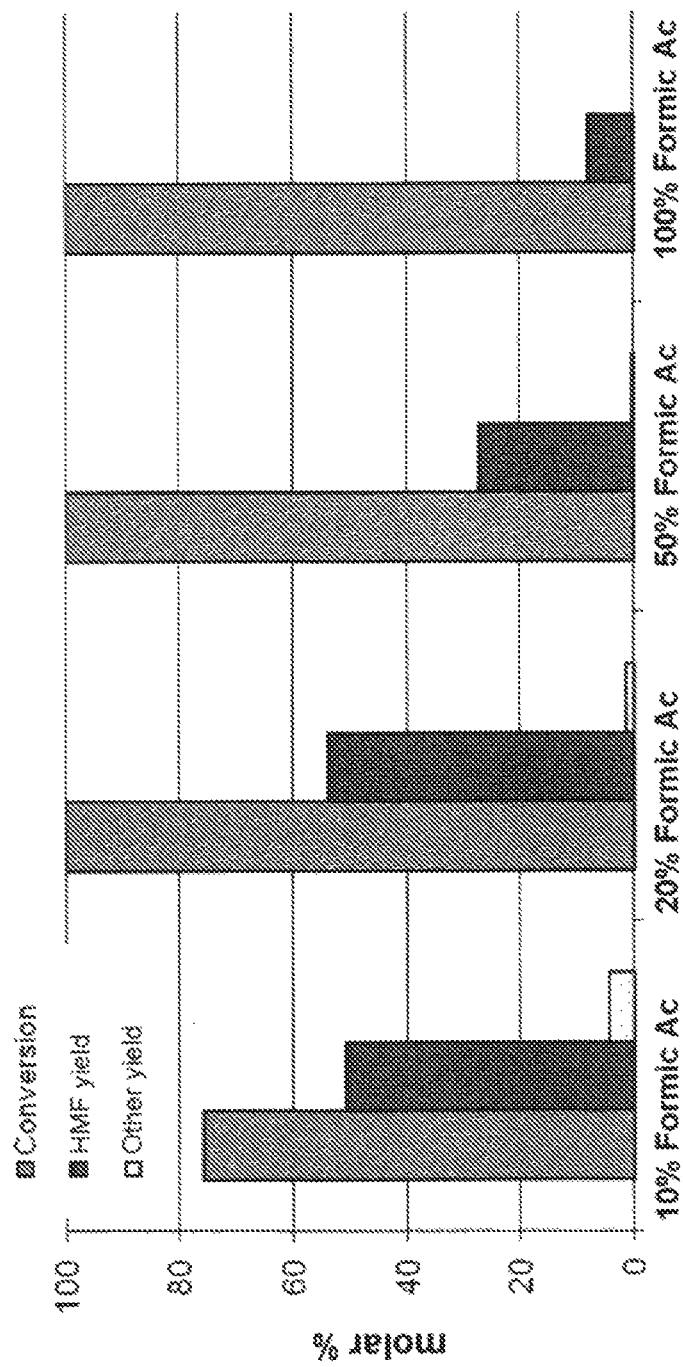
FIG. 4 shows the influence of the formic acid content in the aqueous reaction medium on the conversion of fructose into HMF in the absence of the addition of heterogeneous catalyst at 150° C.

The process was implemented with carboxylic acid in different proportions, namely 5%, 10%, 20%, 30% and 50% by weight of the aqueous reaction medium including fructose and without carboxylic acid. The process was also implemented with a reaction medium including only carboxylic acid and fructose. The results obtained are shown in FIG. 3 and FIG. 4 in order to demonstrate, respectively, the influence of the acetic acid and formic acid content. The results show that, for large quantities of carboxylic acid, the fructose conversion increases, but the HMF selectivity decreases. Thus, when the reaction is implemented with 100% carboxylic acid, a very small quantity of HMF is obtained. The best compromise between fructose conversion and HMF selectivity is obtained for 20% carboxylic acid for acetic acid and 10% for formic acid.

Figure 5:
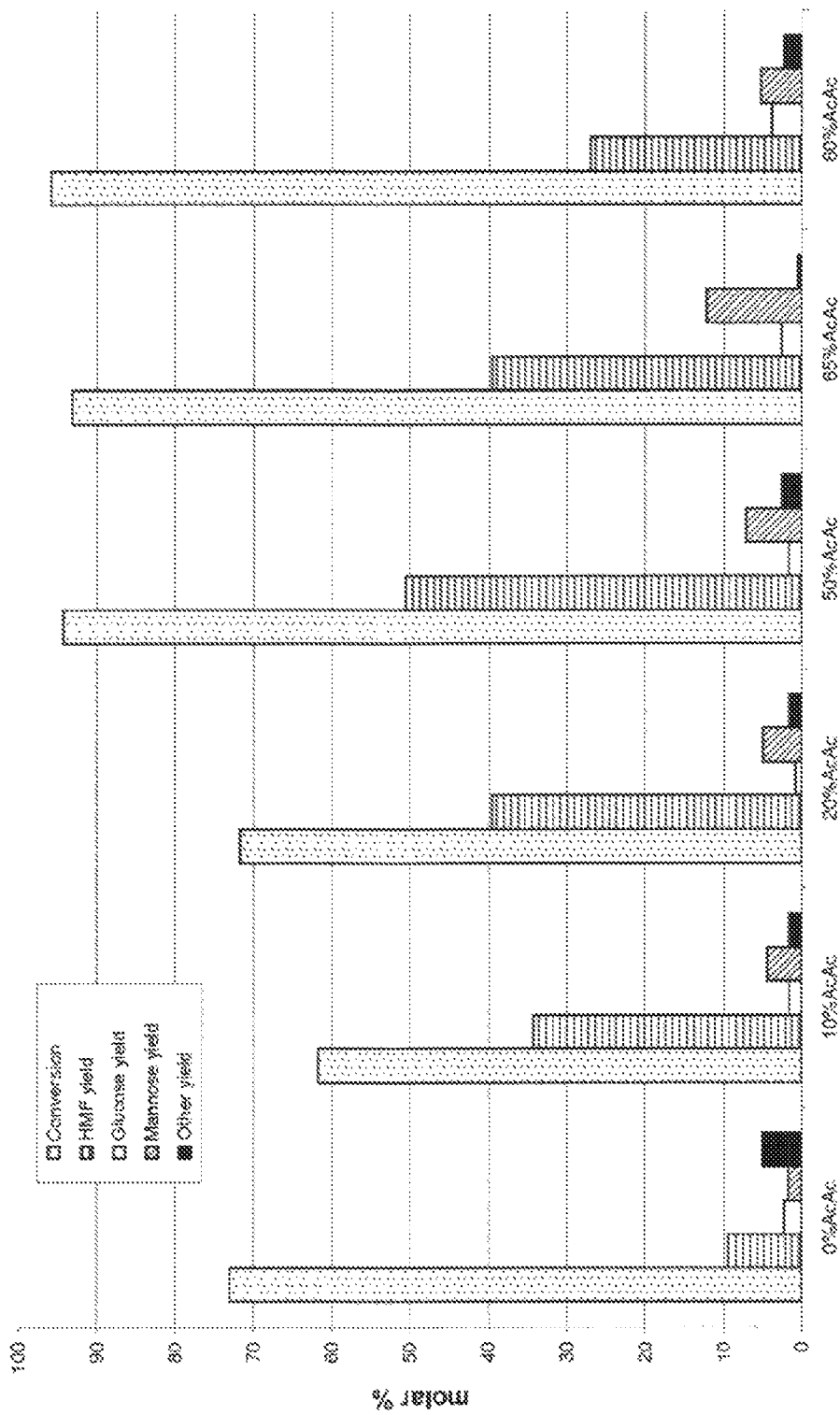
FIG. 5 shows the influence of the acetic acid content in the aqueous reaction medium on the conversion of fructose into HMF in the presence of 5% niobium hydroxide at 150° C.

The same process was implemented with 5% niobium hydroxide with respect to the quantity of fructose. The results obtained are represented in FIG. 5. The results show that, for large quantities of carboxylic acid, the fructose conversion increases, but the HMF selectivity decreases. Thus, when the reaction is implemented with more than 80% carboxylic acid, a small quantity of HMF is obtained.

The best compromise between fructose conversion and HMF selectivity is obtained for 20% acetic acid.

EXAMPLE 4

Influence of the pH of the Starting Reaction Medium

The synthesis of HMF is performed in a 100-ml autoclave. The following quantities are introduced into the reactor: 60 g of distilled water to which HCl for finely adjusting the pH between 3 and 1 and 0.6 g of fructose are added. 2 MPa (20 bars) of helium are introduced into the autoclave. The reaction medium is stirred by means of a magnetic stirrer. The reaction medium is brought to the reaction temperature by means of electrical resistances set at 150° C. After 2 hours of reaction at 150° C., the autoclave is cooled by means of an ice bath. The fructose conversion and the HMF molar yield are determined by HPLC-RID analysis (column: COREGEL 87C).

The influence of the pH at the start of the reaction was studied. For this, the pH of the starting reaction medium was adjusted by adding HCl.

Figure 6:
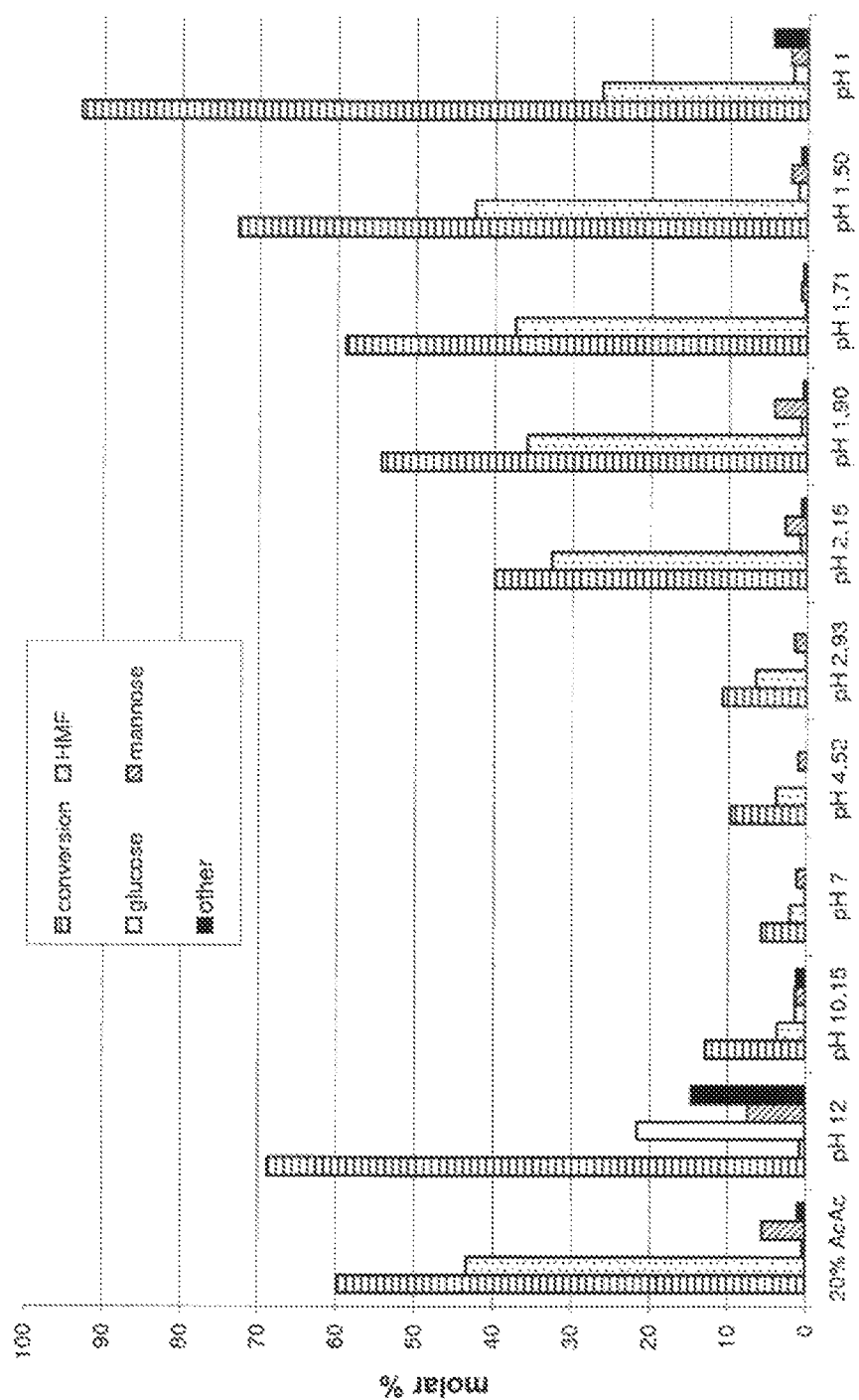
FIG. 6 shows the influence of pH on the conversion of fructose into HMF at 150° C., finely adjusted in the acid pH range, by adding HCl to the aqueous medium.

The results are shown in FIG. 6. The results show that, at low pH, the fructose conversion increases, but the HMF selectivity decreases. The results show that a good compromise between fructose conversion and HMF selectivity is obtained in a pH range of between 1.5 and 2.15, in particular at a pH of 1.71 corresponding to a medium including 20% acetic acid.

EXAMPLE 5

Stability of the HMF

The study of the HMF stability at 150° C. as a function of the composition of the aqueous medium is conducted in a 100-ml autoclave. The following quantities are introduced into the reactor: 60 g of distilled water of 60 g of distilled water adjusted to pH 1.71 by adding HCl or 48 g of distilled water to which 12 g of acetic acid are added. To these solutions, 0.6 g of fructose is added. 2 MPa (20 bars) of helium are introduced into the autoclave. The reaction medium is stirred by means of a magnetic stirrer. The reaction medium is brought to the reaction temperature by means of electric resistances set to 150° C. Samples of the reaction medium are taken at the start of the reaction, then every hour, for analysis. The conversion of the fructose and the HMF molar yield are determined by HPLC-RID analysis (column: COREGEL 87C).

The stability of the HMF was studied in water, in an aqueous medium including 20% acetic acid and in water acidified by HCl at a pH equivalent to that of the 20% aqueous acetic acid solution (i.e. at a pH of 1.71).

Figure 7:
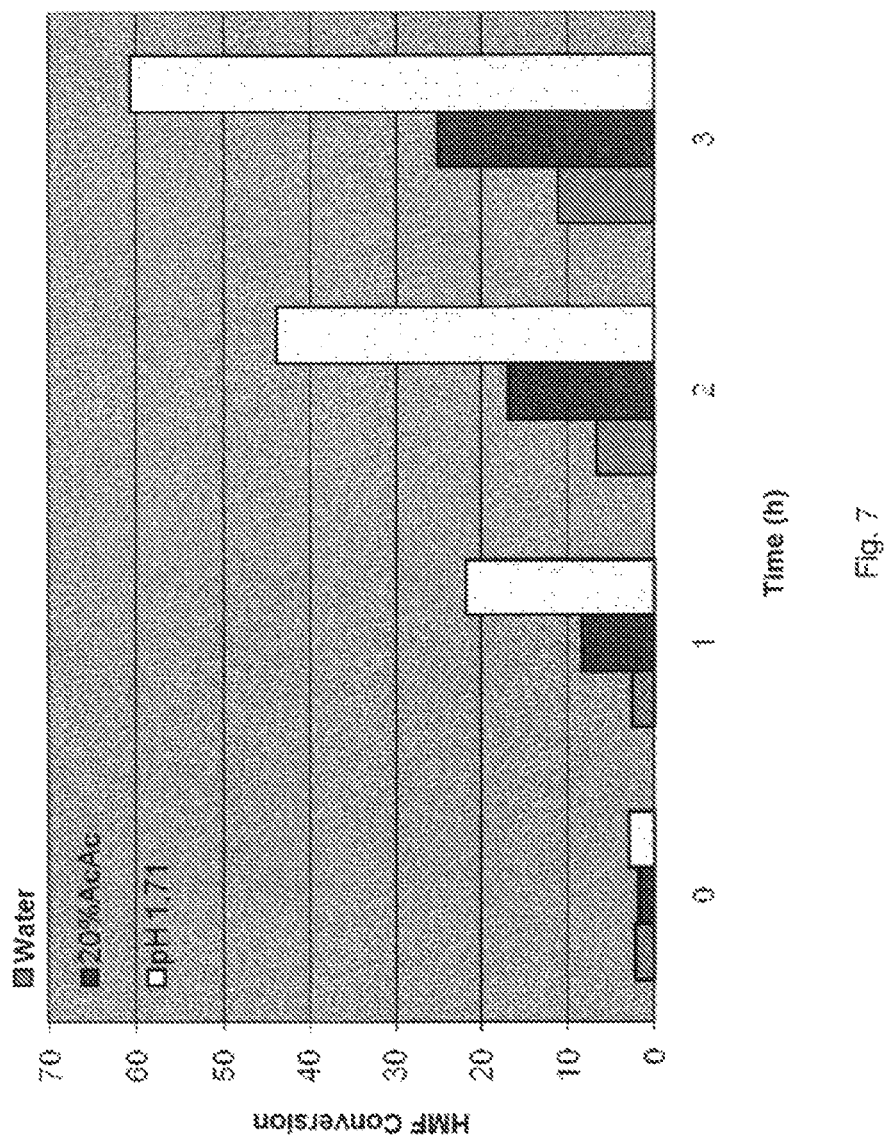
FIG. 7 shows the conversion of HMF in the media: pure water (pH=6.7); 20% acetic acid in water; water acidified by HCl at a pH equivalent to the medium 20% acetic acid in water (pH=1.71).

The results are presented in FIG. 7 and show the HMF percentage converted as a function of time.

The results show a stabilization of the HMF in the aqueous acetic acid medium with respect to the aqueous medium acidified by the HCl mineral acid. The results thus show that the use of carboxylic acid for the preparation of HMF makes it possible to obtain a high hexose conversion and fructose yield while stabilizing the HMF obtained.

EXAMPLE 6

Influence of the fructose content in the starting reaction medium

The synthesis of HMF is performed in a 100-ml autoclave. The following quantities are introduced into the reactor: 48 g of distilled water and 12 g of acetic acid to which 0.6 g of fructose (1%) or 3 g of fructose (5%) or 6 g of fructose (10%) or 9 g of fructose (15%) or 18 g of fructose (30%) are added. The reaction was also produced with 48 g of distilled water and 0.48 g of acetic acid (1%) to which 18 g of fructose (30%) are added. 2 MPa (20 bars) of helium are introduced into the autoclave. The reaction medium is stirred by means of a magnetic stirrer. The reaction medium is brought to the reaction temperature by means of electrical resistances set at 150° C. After 2 hours of reaction at 150° C., the autoclave is cooled by means of an ice bath. The fructose conversion and the HMF molar yield are determined by HPLC-RID analysis (column: COREGEL 87C).

Figure 8:
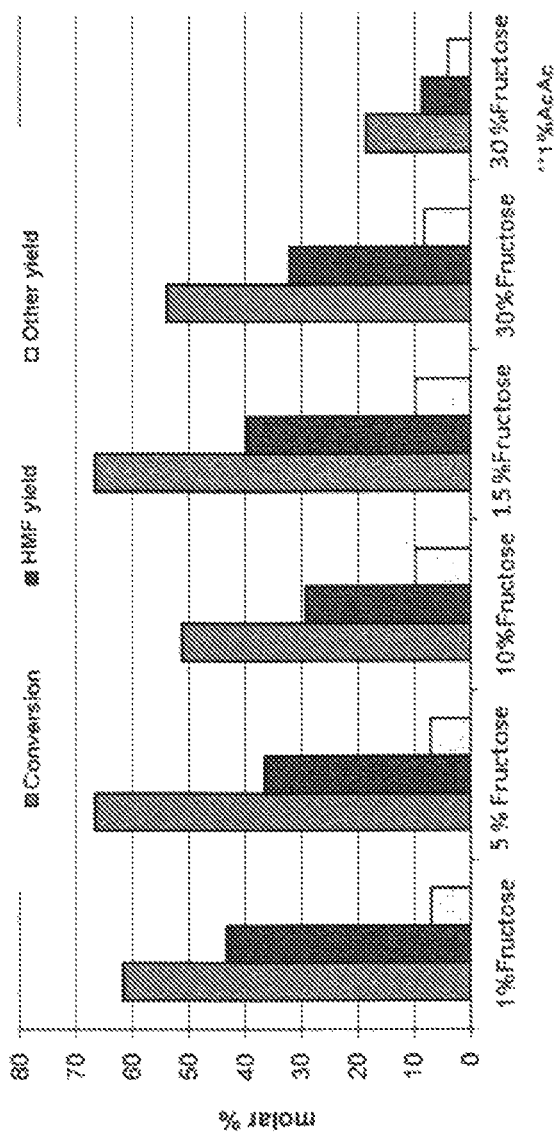
FIG. 8 shows the influence of the fructose content in the aqueous reaction medium containing 20% acetic acid on the conversion of fructose into HMF at 150° C.

The results are shown in FIG. 8. The results show that the fructose conversion and the HMF yield are not significantly affected by the fructose concentration. The results show that the HMF yield obtained from a concentrated fructose solution, in particular 15%, reaches 40%, a value close to the yield obtained from a 1% fructose solution. The fructose concentration is limited by the solubility of the fructose in the aqueous carboxylic acid solution.

EXAMPLE 7

Influence of the Temperature on the HMF Production in a Water-Acetic Acid Medium The synthesis of HMF is performed in a 100-ml autoclave. The following quantities are introduced into the reactor: 48 g of distilled water to which 12 g of acetic acid and 0.6 g of fructose (1%) are added. 2 MPa (20 bars) of helium are introduced into the autoclave. The reaction medium is stirred by means of a magnetic stirrer. The reaction medium is brought to the reaction temperature by means of controlled electrical resistances. The following temperatures are studied: 100° C., 120° C., 150° C. and 180° C. After 2 hours of reaction, the autoclave is cooled by means of an ice bath. The fructose conversion and the HMF molar yield are determined by HPLC-RID analysis (column: COREGEL 87C).

Figure 9:
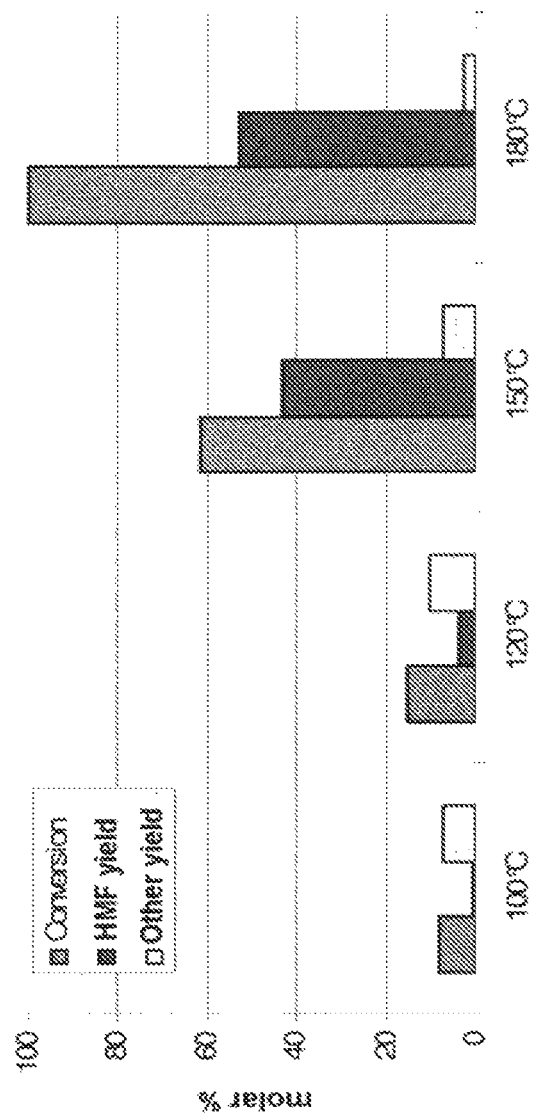
FIG. 9 shows the influence of the temperature on the fructose conversion and the HMF yield in the water-acetic acid reaction medium.

The results are shown in FIG. 9. The results show that the fructose conversion and the HMF yield are low at the reaction temperatures of 100° C. and 120° C. FIG. 9 shows an increase in the fructose conversion and the HMF yield with the increase in temperature. The best compromise between the fructose conversion and the HMF yield is obtained at the temperature of 150° C. It is also observed that at the temperature of 180° C., the fructose conversion is complete and the HMF molar yield reaches 54%.

EXAMPLE 8

Figure 10:
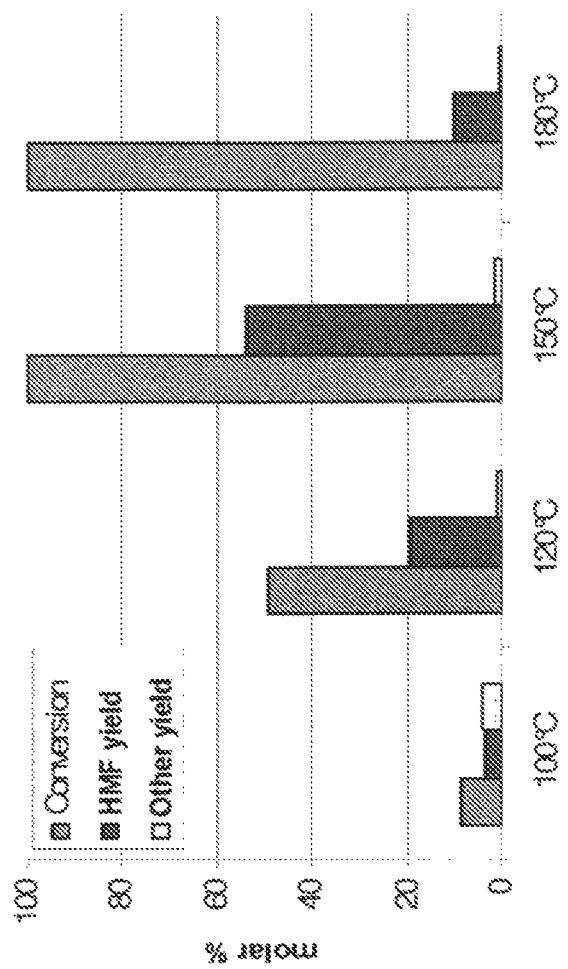
FIG. 10 shows the influence of the temperature on the fructose conversion and the HMF yield in the water-formic acid reaction medium.

Influence of the Temperature on the HMF Production in a Water-Formic Acid Medium The synthesis of HMF is performed in a 100-ml autoclave. The following quantities are introduced into the reactor: 48 g of distilled water to which 12 g of formic acid and 0.6 g of fructose (1%) are added. 2 MPa (20 bars) of helium are introduced into the autoclave. The reaction medium is stirred by means of a magnetic stirrer. The reaction medium is brought to the reaction temperature by means of controlled electrical resistances. The following temperatures are studied: 100° C., 120° C., 150° C. and 180° C. After 2 hours of reaction, the autoclave is cooled by means of an ice bath. The fructose conversion and the HMF molar yield are determined by HPLC-RID analysis (column: COREGEL 87C). The results are shown in FIG. 10. The results show that the fructose conversion and the HMF yield are low at the reaction temperature of 100° C. FIG. 10 shows an increase in the fructose conversion and the HMF yield with the increase in temperature up to 150° C., at which temperature the conversion is complete. At the reaction temperature of 180° C., the fructose conversion is complete but the HMF molar yield is low, 10%. The highest HMF yield, 54%, is obtained at complete fructose conversion, at the reaction temperature of 150° C.

The invention claimed is:

1. A process for preparing 5-hydroxymethylfurfural (HMF) by reacting hexose in water in the presence of carboxylic acid, the carboxylic acid being present in a quantity of 5 to 70% by weight with respect to the total water +carboxylic acid weight.

2. The process according to claim 1, for which the acid is chosen from:
   acids of formula R—COOH, wherein R represents a hydrogen atom or a C1 to C5 alkyl chain, linear or branched, optionally substituted by one or more OH groups, or mixtures thereof.

3. The process according to claim 1, for which the hexose is fructose, glucose or hexose derivatives, wherein said hexose derivatives are selected from the group consisting of cellulose, hemicellulose, starch, lignocellulosic biomass, and paper.

4. The process according to claim 1, for which the hexose is fructose.

5. The process according to claim 1, for which the acid is formic acid, acetic acid, lactic acid, propionic acid, or mixtures thereof.

6. The process according to claim 1, for which the acid is formic acid, acetic acid or a mixture thereof.

7. The process according to claim 1, for which the carboxylic acid is present in a quantity of 10 to 50% by weight, with respect to the total water +carboxylic acid weight.

8. The process according to claim 1, for which the water is present in a quantity of 30 to 95% by weight, with respect to the total water +carboxylic acid weight.

9. The process according to claim 1, further comprising implementing the process in the presence of a solid heterogeneous acid catalyst.

10. The process according to claim 9, for which the heterogeneous acid catalyst is selected from the group consisting of tungstophosphoric acid, sulfated zirconia, acidic cesium salts of tungstophosphoric acid, titanium dioxide, sulfonated carbon, solid carbon functionalized by carboxylic groups, and mixtures thereof.

11. The process according to claim 9, for which the quantity of heterogeneous acid catalyst is between 2 and 100% by weight with respect to the weight of hexose.

12. The process according to claim 1, for which the quantity of hexose is between 0.5% and 30% by weight with respect to the total water +carboxylic acid weight.

13. The process according to claim 1, for which the pH at the start of the reaction is between 1 and 3.

14. The process according to claim 1, conducted at a temperature of between 100 and 200° C.

15. The process according to claim 1, conducted in the absence of organic solvent.

16. The process according to claim 1, conducted continuously.

17. The process according to claim 1, for which the carboxylic acid is present in a quantity of 20% by weight with respect to the total water +carboxylic acid weight.

18. The process according to claim 9, for which the quantity of heterogeneous acid catalyst is between 2 and 10% by weight with respect to the weight of hexose.

19. The process according to claim 1, further comprising implementing the process in the presence of niobium hydroxide.

* * * * *